United States Patent [19]

Eckenhoff et al.

[11] Patent Number: 4,552,561

[45] Date of Patent: Nov. 12, 1985

[54] BODY MOUNTED PUMP HOUSING AND PUMP ASSEMBLY EMPLOYING THE SAME

[75] Inventors: James B. Eckenhoff, Los Altos; John R. Peery, Palo Alto; Felix A. Landrau, Milpitas, all of Calif.

[73] Assignee: ALZA Corporation, Palo Alto, Calif.

[21] Appl. No.: 452,523

[22] Filed: Dec. 23, 1982

[51] Int. Cl.[4] .......................... A61J 7/00; A61M 5/00
[52] U.S. Cl. ..................................... 604/896; 604/131
[58] Field of Search ....................... 604/131, 133, 141, 604/51, 52, 890, 892, 140, 151, 896

[56] References Cited

U.S. PATENT DOCUMENTS

| | | |
|---|---|---|
| 2,589,426 | 3/1952 | Ogle . |
| 3,469,578 | 9/1969 | Bierman . |
| 3,731,681 | 5/1975 | Blackshear et al. . |
| 3,845,770 | 11/1974 | Theeuwes . |
| 3,916,899 | 11/1975 | Theeuwes . |
| 4,282,872 | 8/1981 | Franetzki et al. . |
| 4,320,757 | 3/1982 | Whitney et al. . |
| 4,340,048 | 7/1982 | Eckenhoff . |
| 4,360,019 | 11/1982 | Portner et al. ................. 604/151 X |

Primary Examiner—Stephen C. Pellegrino
Attorney, Agent, or Firm—Steven F. Stone; Paul L. Sabatine; Edward L. Mandell

[57] ABSTRACT

A self-contained body mounted pump assembly for continuously administering a therapeutic agent parenterally. The pump has a transparent top through which the contents can be seen and outwardly flaring sides to provide for comfort, stability and other useful features. The pump assembly is driven by a fluid imbibing, preferably osmotic pump and contains its own source of actuating fluid. Means for superimposing a pulse dose on the tonic flow are also described.

48 Claims, 13 Drawing Figures

BODY MOUNTED PUMP HOUSING AND PUMP ASSEMBLY EMPLOYING THE SAME

FIELD OF INVENTION

This invention relates to pumps particularly pumps adapted to be mounted on the body of a patient for delivering small amounts of beneficial or therapeutic agent over prolonged periods of time.

RELATED PATENTS AND APPLICATIONS

This invention is related to the body-mounted pumps disclosed and claimed in U.S. Pat. No. 4,340,048; July 20, 1982, for Self Driven Hypodermic Injector which is incorporated herein by reference and copending, coassigned patent application of Eckenhoff et al, Ser. No. 344208 filed Feb. 1, 1982, now U.S. Pat. No. 4422848, for Self Driven Infusor and Method of Operation.

BACKGROUND OF THE INVENTION

As disclosed in the above-identified patent and application, there currently exists a need for small, compact self-contained pumps which may be mounted on or in the body and which are capable of delivering precisely controlled amount of various active agents over prolonged periods of time. These devices exist in many forms such as disclosed in U.S. Pat. Nos. 4,320,757; 4,282,872; 3,731,681; and 3,469,578 and produce a significant improvement over the typical hypodermic injection in which a bolus of the active agent is deposited in the body either from conventional hypodermic injectors or specially designed injectors such as shown by U.S. Pat. No. 2,589,426. This bolus must then be gradually absorbed and distributed throughout the body which is a process subject to many individual variances, depending on the physiology of the individual patient. Thus, it is now recognized, particularly with extremely potent active agents such as insulin, interferon or various other chemotherapeutic agents, that it is preferable to have a continuous low rate of infusion of the active agent over a prolonged period of time such as 24 hours or longer rather than 3, 4 or more injections spaced within the same time period. Also, with certain active agents such as insulin, the requirements of the body vary according to conditions. A typical diabetic may have a requirement for a tonic or basal insulin level throughout the day, but after meals may require additional insulin to compensate for physiological changes caused by eating. Thus, a continuous infusion pump would preferably be provided with some means for imposing a pulse dosage on top of the tonic flow.

The infusion pumps disclosed in the above-identified patent and application, represent significant advances in the art since they are compact, reliable, dependable, and relatively inexpensive compared to other prior art devices. In working with such devices we have determined that the human as well as mechanical engineering factors of an infusion pump must be carefully considered in order to gain patient acceptance. These factors cover a wide spectrum of considerations. As discussed by Pickup, et al., "Patient Reaction to Long-term Outpatient Treatment with Continuous Subcutaneous Insulin Infusion" Br. Med. J., Volume 282, pp. 766–768, March 1981, the size of a pump and the psychological impact of wearing the pump on the patient's interpersonal relationships produced the most consistent adverse criticisms. Other factors which must be addressed in order to assure patient acceptance and compliance are ease of operation and handling, minimal adjustments in lifestyle and clothing, concealability, comfort, low cost, maintenance free operation, attractive appearance in use, compact size and ready confirmation of the status of the device i.e., filled, exhausted, pumping, not pumping, for example.

According to this invention, compact, light-weight, maintenance-free, concealable, highly stable and comfortable, easily operated and confirmable body-mounted pump assemblies are provided which are capable of dispensing both water-soluble and water-insoluble beneficial agents at a tonic flow rate or at a tonic flow rate with periodic pulses or with only periodic pulses. These pump assemblies comprise unique housings and unique arrangements of the pump components in combination with the housing and cannula.

It is accordingly an object of this invention to provide housings for body-mounted pump assemblies.

It is another object of this invention to provide body-mounted pump assemblies adapted to administer a predetermined amount of active agent over a prolonged period of time.

It is another object of this invention to provide body-mounted pump assemblies capable of tonic and pulsed delivery.

It is another object of this invention to provide body mounted pump assemblies capable of administering pulsed doses of active agent.

It is another object of this invention to provide simple, inexpensive pump housings and pump assemblies capable of delivering both water soluble and water insoluble active agents.

It is another object of this invention to provide body mounted pumps whose operational status is visually confirmable.

It is another object of this invention to provide self-contained and self-actuated pump assemblies.

It is another object of this invention to provide pump assemblies with a cannula extending from the housing into the portion of the human body whereon the pump assembly is mounted.

It is another object of this invention to provide pump assemblies having a cannula extending from the housing at an angle which minimizes discomfort of insertion and retention.

It is another object of this invention to provide a pump assembly for delivering active agent to a portion of the human body distant from the mounting site of the pump assembly.

It is another object of this invention to provide pump assemblies with modular prefilled drug reservoirs.

It is another object of this invention to provide pump assemblies with reservoirs to be filled at or before the time of use.

These and other objects of the invention will be readily apparent from the following description of the invention with reference to the accompanying drawings, wherein.

DESCRIPTION OF THE INVENTION

Figure 1:
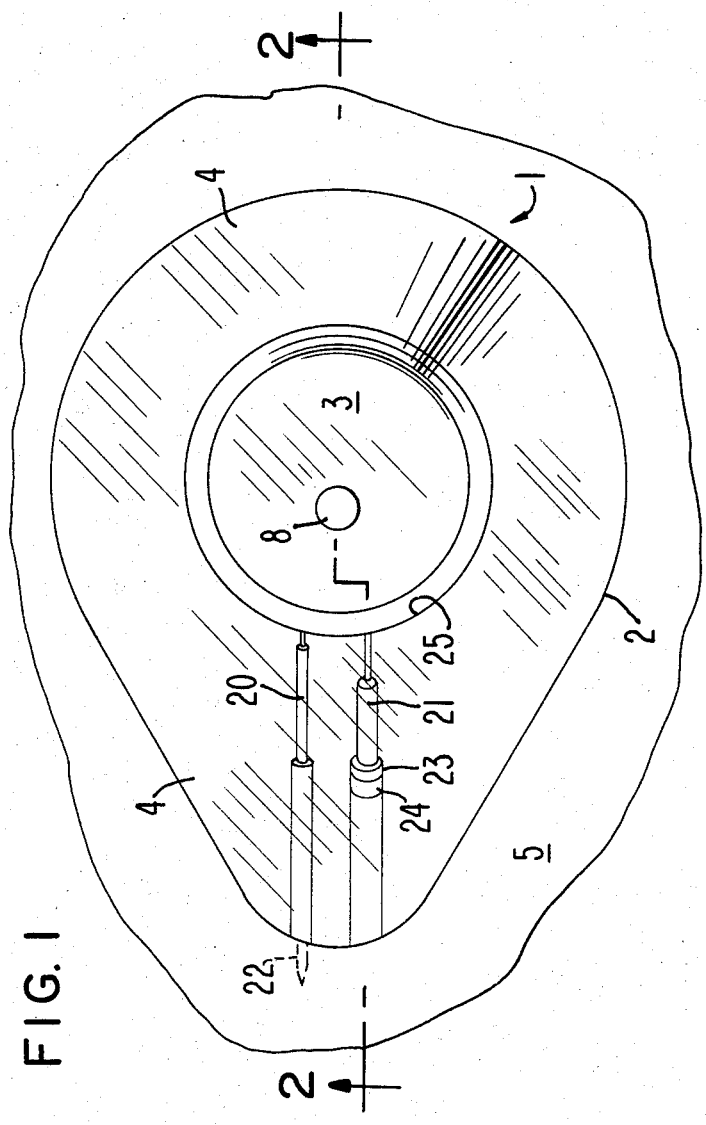
FIG. 1 is a perspective view of a pump assembly according to this invention.
Figure 2:
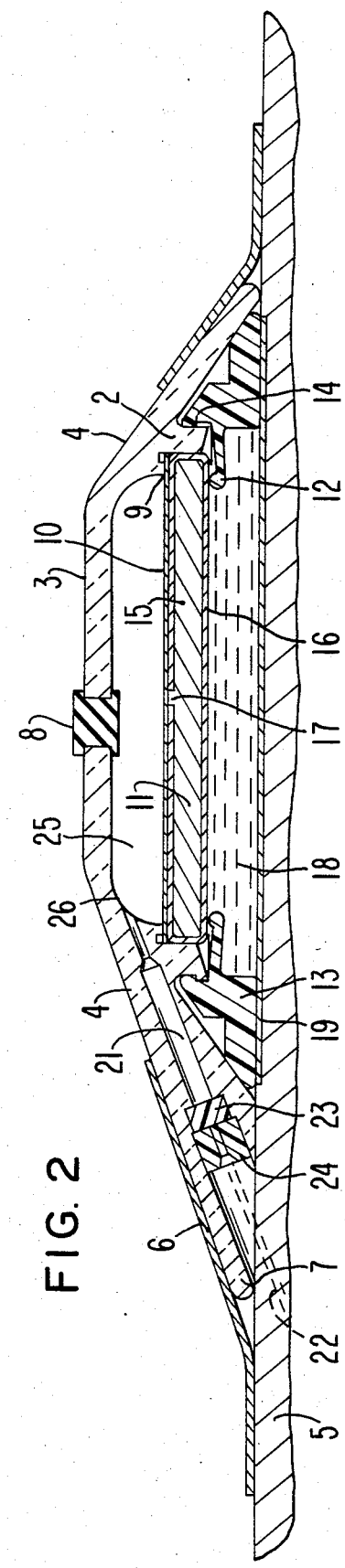
FIG. 2 is a cross-sectional view of FIG. 1 along the line 2—2.

Referring now to FIGS. 1 and 2, a pump assembly shown generally as 1 is mounted on a portion of a human body 5, such as the stomach or thigh, for example, and maintained in place by an annular adhesive overlay 6 (which has been omitted from FIG. 1 for clarity). The pump assembly 1 comprises a housing 2 having a top wall, 3 and a peripheral outer side wall 4 tapering outwardly from said top wall and terminating at its lower end in an annular basal surface 7. The exterior surface of the side wall 4 provides a tapered ramp portion having a wider base than top wall 3 to increase stability, wearability, prevent inadvertent movement after mounting on the skin, provide surface for adhesive attachment, generate a resultant force vector towards the skin, act as thermal insulator and provide increased surface area of the skin for thermal conduction to enhance thermal stability of the pump. The housing 2 is preferably molded in one piece from a transparent material such as polymethylmethacrylate, polycarbonate, polysulfone, PVC, medium-to-high density polyethylene or other transparent or semi-transparent high modulus polymers which are heat resistant, chemically inert and capable of withstanding sterilization conditions. The transparency of top wall 3 permits visual confirmation of the operational status of the pump as will be more fully explained hereafter. Top wall 3 may, in certain embodiments of this invention, be provided with an optional septum 8 inserted through a hole in the top wall in sealing engagement therewith and adapted to be resealingly pierced by a needle for filling or for introduction of a pulse generator to add to the constant tonic flow for which the pump is designed.

The interior of housing 2 contains a hollow receptacle defined between the interior surface of top wall 3 and the interior side surfaces of housing 2. An internal annularly extending shoulder 9 is provided in the receptacle, on which rests displacement member 10 and a fluid imibibing pump 11, both of which are maintained in place by spring flange 12 on compression ring 13 which is snappingly engaged to housing 2 at annular groove 14. Spring flange 12 is biased to exert pressure against the fluid imbibing pump 11 to maintain a fluid tight seal between the pump 11 and the displacement partition 10 and the shoulder 9. Displacement partition 10 is formed of a relatively low modulus, impermeable material such as styrene-butadiene block copolymers, natural rubber, latex rubber, silicone rubber, isoprene rubber, polyurethane rubber or mixtures thereof, for example.

Figure 3:
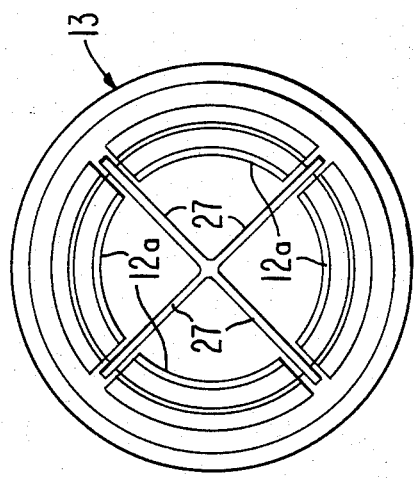
FIG. 3 is a plan view of component elements of the embodiment of FIG. 2.

As shown more clearly in FIG. 3 compression ring 13 is provided with reinforcing means 27 shown as a cross-shaped spider adapted to support and stiffen fluid imbibing pump 11 to prevent it from bending downwardly in reaction to pressure generated between pump 11 and displacement partition 10 during operation. Spring flange 12 is formed in independently movable segments 12a, b, c and d and reinforcing means 27 may either be formed integrally with member 13 or may rest in grooves formed between the segments 12a, b, c and d.

Various types of fluid imbibing pumps are known to the art as described in the above identified patent and application and are adaptable for use herein. In view of their simplicity and low cost, however, the preferred embodiment utilizes an elementary osmotic pump. An elementary osmotic pump consists of an osmotically active water soluble material 15 such as common salt, contained within a rigid semipermeable membrane 16 provided with one or more outlets 17 all as disclosed in U.S. Pat. Nos. 3845770 or 3916899 to Theeuwes et al which are incorporated herein by reference. Since the fluid pumped from outlet 17 does not leave the system the maximum size of outlet 17 is not critical and could even be equal to the entire top surface although this may not practical from a manufacturing standpoint. A source for the fluid to be imbibed by the osmotic pump 11 is disposed within the volume defined by compression ring 13 which is preferably a simple hydrogel 18 maintained within the pump assembly and preferably separated from the skin by an impermeable, preferably flexible backing 19.

The side wall 4 of housing 2 may be provided with passageways 20 and 21 which provide fluid communication from a point proximate the basal surface 7 of the wall to the chamber 25 formed between the displacement partition 10 and the interior surface of transparent top wall 3. One of these passageways 20 is provided with a cannula for delivery to a remote location or a needle 22 adapted to pierce the skin preferably at an angle in the range of from 10°–30°, preferably 15, and the other of said passageways is provided with a piercable resealable septum 23 maintained in place by tight-fitting fill port plug 24 to permit charging the displacement chamber 25 with the material to be dispensed. The interface between the interior surface of top wall 3 and the interior surface of side wall 4 is preferably radiused as shown at 26 to eliminate the possibility of air being trapped in the corners and to facilitate complete expulsion of the entire contents of the displacement chamber 25 as will be explained hereinafter. As shown in FIG. 1 and 2, the housing configuration is assymetric, however the device can also be symetrical which would entail the legs of the ramp portion on all sides of the device being the same angle to the horizontal.

It should be noted that embodiments utilizing septum 8 could be fabricated without passageway 21 using self-sealing septum 8 to charge the device as will be explained hereafter.

The configuration shown in FIGS. 1 and 2 presents several unique advantages. First of all, the chamber 25 containing the material to be pumped is at the top portion of the assembly which permits direct viewing of the contents through the transparent top wall 3. The side walls taper outwardly to provide a stable platform on the body both alone and in combination with the lower surface of the compression ring 13. In addition to being more volume efficient than a cylindrical housing of the same basal diameter the sloping side wall also possess the unique advantage of being capable of converting impacts on the side wall into a force on the housing which has a downward component. This feature together with the angular insertion of the needle under the skin provides for greater comfort in use to the patient and reduces the likelihood of inadvertent dislodgement of the pump or needle.

Since the flow rate of an osmotic fluid imbibing pump varies to some extent with temperature, the sloping configuration also contributes to the maintenance of a relative constant temperature approximating body temperature. The large basal surface area provides good thermal conduction from the skin and the hydrogel and other pump components act as a heat sink to maintain thermal equilibrium. In addition the sloping sides provide a large surface area for the adhesive overlay which also insulates the sides leaving only the unexposed substantially smaller exposed top surface as the primary path of heat loss. If desired the adhesive overlay could have a central transparent area which could be placed over the top surface to further minimize heat loss in those circumstances where the pump is mounted on an exposed body surface instead of concealed under the clothing. It should be understood however, that while the design of the pump assembly of this invention facilitates direct insertion of the needle under the skin of a patient at the situs of the pump, the pump outlet could just as easily be connected by a cannula to a catheter or IV-line which is inserted into the body at a spot remote from that on which the pump is mounted.

The pump of this invention is preferably employed for the administration of fluid active agents which require approximately 5 milliliters or less per day. This administration rate is typical of such drugs as insulin, interferon, various polypeptides and oncotic agents which are generally administered through the skin into the subcutaneous space. With this design approach, it can readily be seen that a very small compact pump can be provided which can administer not only a single day's supply, but a multi-day or weeks supply. Five milliliters per day can be delivered by a flow rate of only slightly more than 0.2 milliliters per hour, a delivery rate well within the capability of the elementary osmotic pumps described in the above-identified patents. Thus, for example, in one embodiment a displacement chamber 25 approximately 2.77 cm in diameter and 0.30 cm deep will have a volume of about 1.6 cc which will be a 3 day supply of U-100 insulin.

To utilize the device of FIGS. 1 and 2, the components of the assembly 1 would normally be delivered to the pharmacist in a partially assembled and sterile condition. Various models can have different flow rates determined by the type of drug, the dosage of the drug and the specific design of the fluid imbibing or osmotic pump 11. It is contemplated that the partially assembled device would comprise the housing 2 having the needle 22, fill port plug 24 and septums 23 (and 8, if used) preassembled with the remaining elements shown in FIG. 2 also in sterile packages.

It is contemplated that uniformly sized osmotic pumps having differing outputs will be available to the pharmacist so that the desired flow rate for any particular drug can be obtained. Further adjustment of the flow rate is possible by varying the osmotic properties of the liquid component of the hydrogel, by placing another fluid permeable membrane in series with the osmotic pump or by placing an impermeable layer in series to partially occlude the osmotic pump. The pharmacist would place expansible displacement member 10 on shoulder 9, insert the proper osmotic pump 11 and additional membranes if needed and snap the assembly together with snap ring 13.

The pharmacist would then fill the drug reservoir through septum 23 by means of a sterile needle with the appropriate concentration of the fluid active agent composition to be dispensed. The absence of air is verified by visual observation through transparent top 3 and by the emission of a steady liquid stream from needle 20. Drug in displacement chamber 25 is now effectively isolated from the environment by the displacement partition 10, the osmotic pump 11, and the seal produced as a result of the pressure exerted by the spring bias means 12 against shoulder 9.

This system could then be delivered to the patient or his physician together with adhesive overlay 6, an impervious backing film 19 and a supply of hydrogel, in a tube, for example. When ready for use, the hydrogel 18 would be filled into the volume defined between snap ring 13 and the surface of pump 11 the backing member 19 would be applied to the base and maintained thereon preferably by a contact adhesive applied to the upper face of backing member 19.

While the pump is being charged, the injection site can be prepared in the conventional manner. The charging process normally may take from about 3 to 8 minutes depending on fluid, osmagent and membrane thickness. The actual time will be that which is required for the liquid component of source 18 to diffuse through semi-permeable wall 16 and dissolve the osmagent 15 in pump 11. Steady state is reached when the saturated solution formed within pump 11 is emitted steadily from outlet 17 to cause displacement partition 10 to be steadily forced into chamber 25 to displace the contents thereof through passageway 20 and cannula or needle 22. When a steady flow of fluid is seen to be emerging from the needle it is inserted under the skin and overlay 6 applied to hold it in place.

It is preferred to use overlay 6 in conjunction with an adhesive on the base of the device because the overlay serves to protect and cover the injection site thereby reducing the likelihood of subsequent infection as well as to act as a thermal insulation. Overlay 6 may also be a carrier for a topical antiseptic, antibiotic or local anesthaetic or other agent to reduce the likelihood of infection or discomfort.

The patient installation procedure is no more complicated than the current practice by which patients self-administer insulin injections. Since one pump insertion can continuously deliver insulin for the same time period that now requires many pulse injections, the advantages of this system are readily apparent. In addition, when a pulse dosage form is used in combination with the pump assembly, pulse dosages can be administered to supplement the tonic basal delivery rate of the pump without the necessity of an additional puncture for each pulse. The pump assembly is also sized to be easily concealed under the clothing and to present a relatively innocuous and non-disfiguring appearance to assist in the subjective acceptance of the device by the user. The 10–30 needle angle (preferably about 15) has been found experimentally to be subjectively more acceptable to the patient in terms of minimizing discomfort on insertion and during continuous use than shallower or steeper angles.

Figure 11:
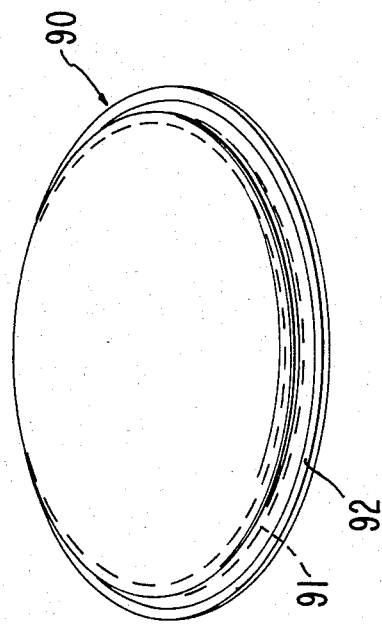
FIG. 11 is perspective view of a pre-filled dosage form according to the invention.
Figure 12:
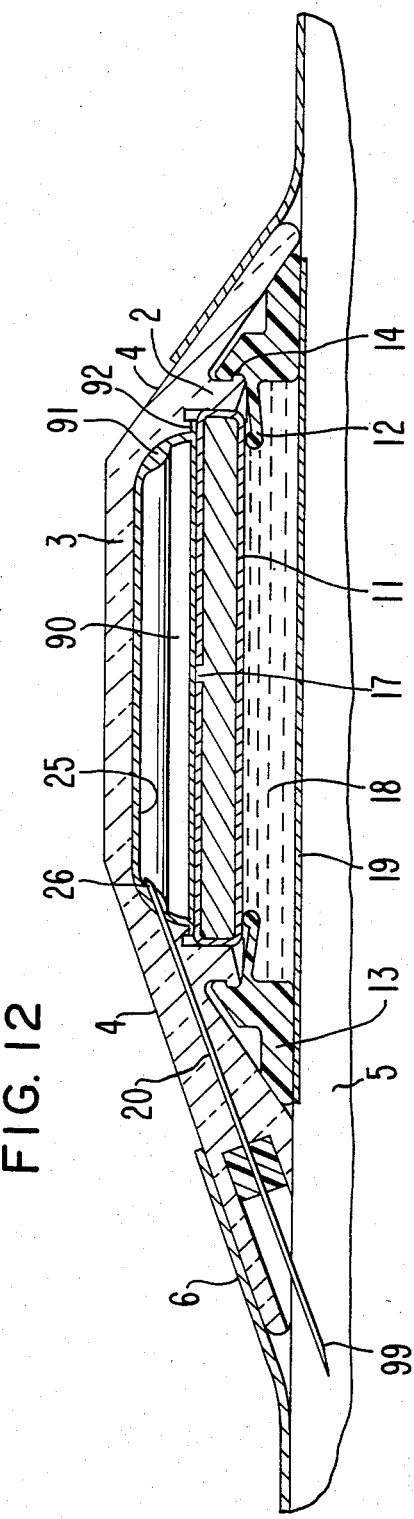
FIG. 12 is a cross section view of an embodiment of the pump assembly of this invention utilizing the dosage form of FIG. 11.

While the above embodiment contemplates the filling of the pump assembly through fill port 21, it is also contemplated that the fill port 21 can be eliminated and the material to be dispensed provided in modular form. Thus, for example, by reference to FIGS. 11 and 12, (like reference members corresponding to those of FIGS. 1 and 2) the material to be dispensed may be provided in prepackaged form together with an osmotic pump which is precalibrated to produce any desired flow rate. Such a modular system would consist of a collapsible container 90 made from an impermeable, low modulus elastic material similar to that which would be used to manufacture displacement membrane 10. Container 90 is sized to fit securely within the chamber 25 in the upper portion of the interior of housing 2. A preferred embodiment of container 90 would be provided with an annular thickened welt 91 which is located so as to be aligned with outlet port 20 in the housing 2. This welt would be adapted to function as a resealable septum to permit filling of container 90 and subsequent withdrawal of the contents therefrom. In addition, container 90 is preferably provided with an annularly extending lip 92 adapted to seat on shoulder 9 in the same manner as displacement member 10 to form a fluid tight seal against shoulder 9. In order to operate the pump assembly, a double-ended hollow needle 99 could be inserted into outlet port 20 with the inner end being of sufficient length to pierce welt 91 and provide a fluid passageway from the interior of container 90 to the exterior of the pump. In this embodiment, the prepackaged drug containers and suitable osmotic pumps would be provided in sterile form to the pharmacist who would then assemble the appropriate combinations. This would be provided to the user with a double-ended needle which would be inserted in the outlet port at the same time that the fluid source 18 is added to prepare the device for operation as described above.

Figure 4:
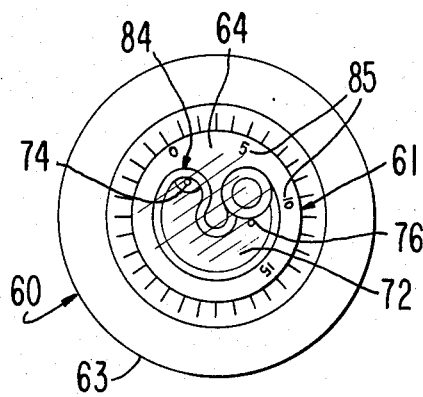
FIG. 4 is a top-view of a rotary syringe pulse dosage form which may be used in conjunction with a pump assembly according to this invention.
Figure 5:
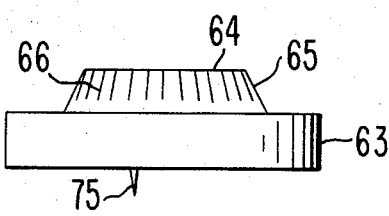
FIG. 5 is a side view of the device of FIG. 3.
Figure 6:
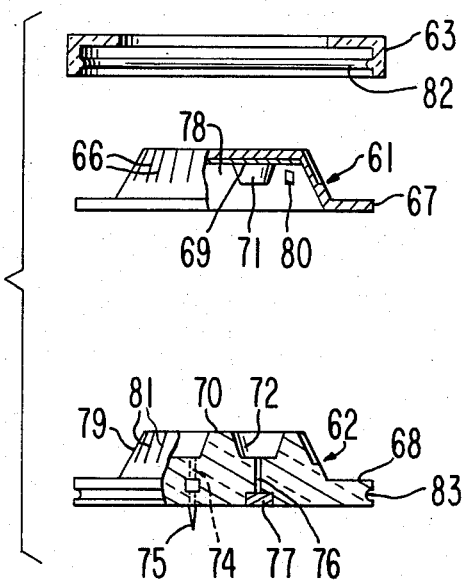
FIG. 6 is a side, exploded view partly broken away of the elements of the device of FIGS. 4 and 5.

Referring now to FIGS. 4, 5, 6 and 7, a rotary syringe injector of the type disclosed and claimed in copending, coassigned patent applications of Eckenhoff and Peery for Rotary Syringe filed 12-23-82, Ser. No. 452,552, is shown which may be either used alone to administer manually instigated pulse dosages or may be mounted on or formed integrally with pump housings according to this invention to provide manually instigated pulse dosages supplementing the basal delivery rate. As described in their patent application and as shown in FIGS. 4, 5 and 6 herein, a rotary syringe 60 comprises a cap 61 preferably formed at least in its upper portion of a transparent material, a base member 62, which may also be formed from a transparent material, and a snap ring 63 adapted to maintain the cap 61 and base 62 in rotational interrelationship. In FIG. 4, cap 61 and base 62 are formed from transparent materials such that the interior structure of cap 61 and base 62 are visible through the transparent top 64 of cap 61. The side wall 65 of cap 61 preferably tapers outwardly from top 64 and is knurled at 66 to facilitate rotation of the cap with respect to base 62. The base of cap 61 terminates in an annular extending flange 67, the top surface of which is flat and adapted to rest on a similarly located annular flange 68 formed about the periphery of base 62. The inner portion of top 64 has mounted thereon a circular elastomeric gasket 69 which is preferably substantially coextensive with the top surface 64 and of sufficient thickness to provide a fluid tight seal between the interior of cap 61 and the top surface 70 of base 62. An elastomeric plug 71 depends from gasket 69 and may either be formed integrally therewith or otherwise firmly attached thereto. Plug 71 is configured to be in fluid sealing relationship to the side and base surfaces of reservoir 72 which is defined by an annular recess formed by machining or molding or otherwise in the top of base member 62. The ends of reservoir 72 are adapted to conform to the exterior of plug 71 in fluid sealing relationship and the inner and outer side walls are defined by semicircular walls having a common center such that upon rotation of cap 61, piston 71 may traverse from the position shown in FIG. 3 to the opposite end of he reservoir over outlet port 74 in a fluid sealing manner to thereby displace through outlet port 74 formed in body 62 and through a needle or other fluid conduit 75, the fluid contents of the reservoir 72. An inlet port 76 is also provided at the opposite end of the reservoir 42 and spaced therefrom by at least the distance of the diameter of the base of plug 71 to permit the filling of reservoir 72 through resealable septum 77. Needle 75 is maintained in place in the outlet port 74 by screw threads or a frictional fit or any suitable means and in one embodiment is adapted to be aligned with septum 8 in the top of the pump assembly of FIG. 1, for example.

The interior side wall 78 of cap 61 and the exterior side wall 79 of base member 62, are parallel so that cap 61 may be nested on base 62 with side walls 78 and 79 in close fitting relationship. A plurality of preferably uniformly spaced pawls 80 are preferably formed integrally on internal side wall 78 and are adapted to engage a multiplicity of ratchet teeth 81 formed on the exterior side wall 79 to form a ratchet mechanism which permits rotation of the cap 61 with respect to the base 62 only in one direction. In the embodiment shown this is the clockwise direction such that piston 71 will rotate from the position shown in FIG. 3 to the opposite end of reservoir 72 thereby forcing the fluid contents which are in reservoir 72 out through outlet port 74. To assemble the device, cap 61 would be placed on base 62 with flange 67 resting on flange 68 and snap ring 63 slipped over cap 61 and held in place by means of annular tongue 82 which is engaged in annular groove 83 around the periphery of the base member. Snap ring 63 is adapted to maintain the cap 61 on base 62 with sufficient pressure such that gasket 69 within the top of cap 61 forms a fluid tight seal between the top of base 62 to prevent any fluid within reservoir 72 from escaping from the reservoir other than through outlet 74. A suitable medical lubricant such as Dow Corning 60 Medical Fluid may be applied to the abutting surfaces 68, 67 and the top of base 62 to facilitate the rotational motion of the cap 61 to the base without binding or the material used to form gasket 69 can be selected to have the desired slip characteristics. The rotable syringe can be calibrated by appropriate selection of the size and spacing of the teeth 81 such that the rotation of the cap one notch will discharge a predetermined quantity of fluid. To facilitate use, cap 61 and base 62 can be provided with suitable marking indicia such as arrow 84 molded or printed on cap 61 and indicia 85 printed or molded on the periphery of the upper surface of base 62 and visible through the transparent top 64 of cap 61 such that the user will have a visual indication of quantity of the material consumed and of the remaining amount in the injector. When the rotary syringe is to be mounted on the top of a pump assembly, an adhesive coating could be applied to the lower surface of base 62 to maintain the pulse dosage form in place and prevent rotation with respect to pump assembly when cap 61 is rotated. In use, the material desired to be dispensed would be filled into reservoir 72 by introduction from a suitable needle inserted thrugh septum 77 and charged into the reservoir until a steady stream of fluid is emitted through needle 75 to eliminate any air from the chamber. The needle 75 could then be inserted through septum 8 in a device such as shown in FIGS. 1 or 2 after it had been charged and the entire assembly mounted on the skin as described above. When a pulse dosage is required on top of the tonic flow emitted from the pump, the user would merely rotate cap 61 until the desired dosage has been administered.

Figure 7:
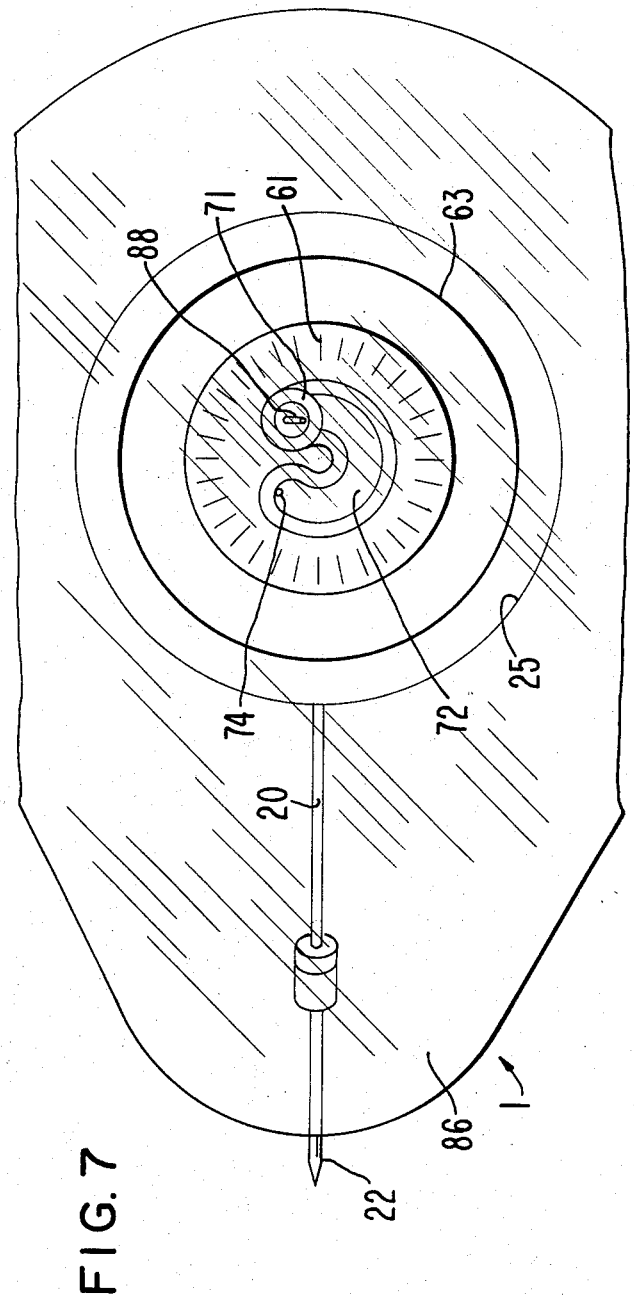
FIG. 7 is a plan view of another embodiment of this invention in which a pulse generator is formed integrally on the pump assembly.
Figure 8:
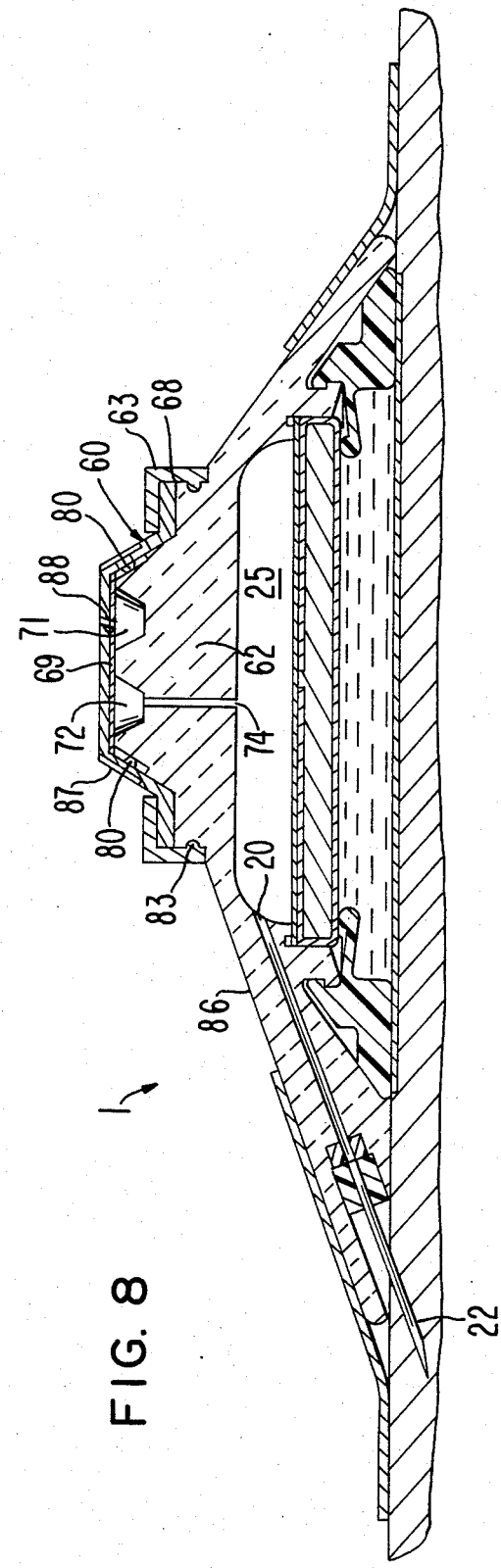
FIG. 8 is a cross section through the embodiment of FIG. 7.

While FIGS. 4, 5 and 6 show the rotary syringe as a component separate from the pump assembly of this invention, it is also possible, and a preferred embodiment of this invention, to utilize the rotary syringe formed as an integral portion of the pump assembly of this invention. This is readily accomplished as shown in FIGS. 7 and 8 in which the base element 62 in FIGS. 4, 5 and 6 is formed as an integral part of a housing such as shown in FIG. 2 for example. Referring now to FIGS. 7 and 8, in which like reference numerals refer to like elements in preceeding Figures, another embodiment of pump assembly 1 is shown. Assembly 1 comprises a housing 86 which differs from the housing 2 shown in FIGS. 1 and 2 for example, in that it is provided only with outlet port 20 instead of the inlet and outlet ports and instead of the upper face of the housing terminating in a transparent flat portion 3 as shown in FIG. 2, it is formed ito a configuration corresponding to that of base 62 of rotary syringe 60. Accordingly, the upper portion of housing 86 is provided with an annular shoulder 68 and a circumferential snap ring groove 83 and a semicircular depression forming reservoir 72 having outlet port 74 extending from one end thereof and into fluid communication with the upper portion of displacement chamber 25. A cap 87 corresponding to cap 61 of FIG. 4 and provided with gasket 69 and plug 71 is maintained on shoulder 68 by means of snap ring 63. In this embodiment cap 87 is provided with port 88 located over plug 71 and inclined to direct a filling needle through the top and side of plug 71 and into communication with chamber 72, plug 71 being formed from a self-sealing elastomeric material so that it will function both as a displacement piston and as a resealable septum. Alternatively, the filling passageway 21, with resealable filing septum and port 23 and 24 can be constructed to directly communicate with reservoir 72 directly in front of piston 71 thereby bypassing reservoir 25, said reservoir 25 being in fluid communication with reservoir 72 through port 74. The internal mechanisms of the ratchet teeth and pawls as well as the indicia shown in FIGS. 3-5 are used for the same functions as in FIGS. 3-5, the latter being omitted for clarity in FIG. 6. In the embodiment shown both the pulse generator and the main drug reservoir can be filled by introducton of the needle through port 88 which will fill not only reservoir 72, but also displacement chamber 25 through port 74.

Figure 10:
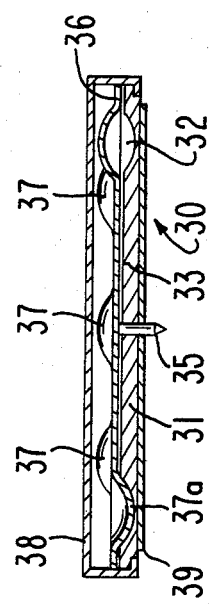
FIG. 10 is a cross section through line 10—10 of FIG. 9.
Figure 9:
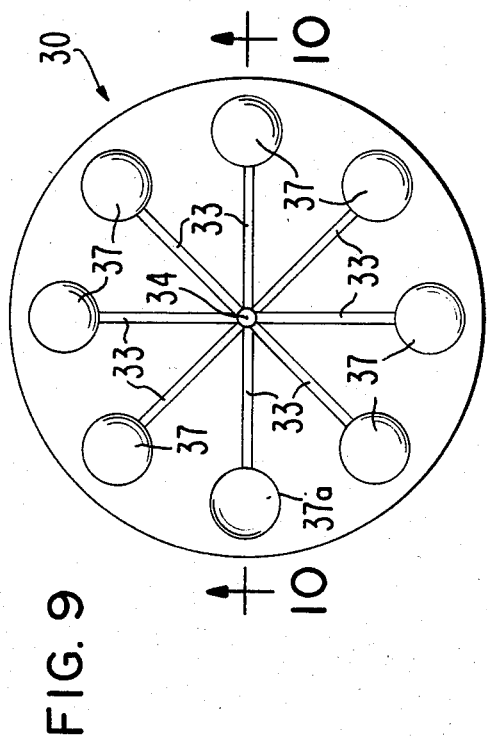
FIG. 9 is a top view of another pulse dosage form that may be used in conjunction with the pump assembly of this invention.

Referring now to FIGS. 9 and 10 a pulse dosage delivery device such as is disclosed and claimed in copending coassigned patent application of Peery and Eckenhoff for Multiple Fluid Pulse Dispenser filed 12-23-82, Ser. No. 452,522 is shown which may be used in combination with the pump housing of this invention. As described in that patent application, such a pulse dosage form 30 would consist of a base member 31, provided with a multiplicity of indentations 32 which may be of the same or different sizes and a fluid conveying groove 33 associated with each indentation providing fluid communication to a common outlet 34 which in this embodiment is shown as a fine gauge needle 35 which extends through the base 31 and is of a length just sufficient to penetrate septum 8 in the top of a pump housing such as shown in FIG. 1 and 2. Overlaying base 31 is a displacement member 36 which in its initial configuration is provided with a mulitiplicity of prominences 37 sized and located to coincide with the indentations 32 in base member 31. Displacement member 36 is bonded or otherwise sealingly affixed to base 30 so that fluid flow from the depots defined between indentations 32 and prominences 37 can only occur through grooves 33 to outlet 34. The displacement member is preferably permanently deformable such that on depression of prominence 37, it will permanently invert and conform precisely to the interior surface of indentation 32 as shown at 37a and force the contents of the depot through passageway 33 and out the needle 35 and into the displacement chamber 25 of housing 2. Pulse dosage form 30 is preferably provided with a cap 38 (FIG. 10) which may be in frictional, threaded or locked engagement, for example, with the side of base 31. The lower surface of base 31 is preferably provided with a contact adhesive 39 to provide for permanent mounting on the top of housing 2. Preferably all of the elements comprising pulse dosage form 30 would be transparent such that even with the dosage form in place, it is possible to visually observe the operational condition of displacement chamber of the pump assembly to verify operation. Also it is apparent that such a pulse dosage form could be an integrated part of the housing in such the same manner as the rotary syringe of FIG. 8. It should be noted that the dosage form 30 is only generally described herein. Details of construction and method of operation are disclosed in depth in the aforemention U.S. patent application. While we have disclosed specific pulse dosage forms usable in conjunction with the pump assembly of this invention, it should also be readily apparent that other means for imposing pulse dosages on the tonic flow rate can be used. Thus for example a hypodermic syringe needle can be inserted through septum 8 to inject a pulse dosage or septum 8 could be replaced by displacement piston assembly such as is disclosed in U.S. Pat. No. 4,340,048. Also other pulse dosage generators could be formed as an integral part of the housing assembly.

Figure 13:
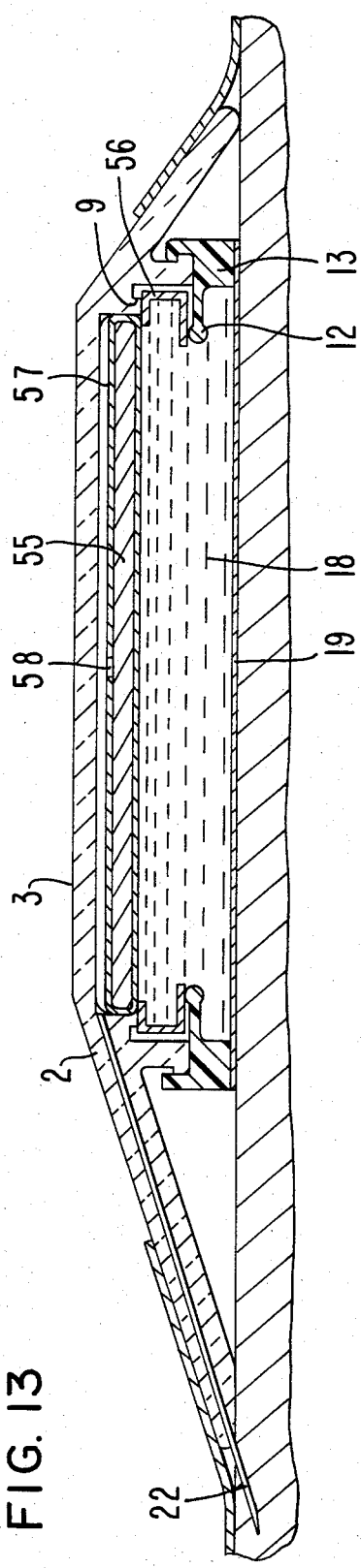
FIG. 13 is a cross section through another embodiment of pump assembly utilizing the dosage form of FIG. 12 according to this invention.

Referring now to FIG. 13, another embodiment of the invention is shown in which rather than utilizing a positive displacement element to force the drug from the reservoir under the influence of a working fluid generated by a fluid imbibing pump, an osmotic pump is used to both generate and pressurize the material active agent to be dispensed. The same housing used for the embodiment of FIGS. 1 or 2 may be used in this embodiment of the invention and for convenience, the same elements shown in FIGS. 1 and 2 are utilized in FIG. 2 with displacement member 10 and pump 11 being replaced by spacer element 56 and fluid imbibing pump 55. While any fluid imbibing pump mechanism can be employed to form pump 55, the simplest and preferred mechanism for delivering a water-soluble drug consists of an elementary osmotic pump with the drug being the osmagent as described in the Theeuwes et al patents noted above. Low solubility or insoluble drugs can be dispensed from other types of fluid imbibing pumps as is known to the art but with this invention such compositions would be more conveniently dispensed from the embodiment of FIGS. 1 and 2.

In the embodiment of FIG. 13 the pump 55 consists of a semipermeable membrane 57, having an outlet orifice 58, enclosing an osmotically active composition such as a water-soluble drug or a water insoluble drug mixed with other osmotically-active materials sufficient to dispense the contents of pump 55 upon exposure to water, all as is known to the art. In this embodiment, pump 55 is located within the portion of the receptacle which formed the displacement chamber 25 in FIGS. 1 and 2. In order to miminize the void volume and the start-up time for the device, pump 55 is sized to be received in the housing 2 abutting the curved interface between the inner surface of top wall 3 and the side wall of the receptacle. In order to maintain a fluid tight seal, a hollow spacer element 56 may be used, configured to be sealingly received between shoulder 9 and leaf spring means 12 with its lower portion being contacted by spring 12. In operation, the hydrogel would be filled into the center of spacer means 56 as well as in the lower portion of the receptacle and maintained in place by impermeable backing member 19. In this embodiment of the invention, after assembly of components 2, 13, 56 and 55, it would be delivered to the physician or patient. Prior to insertion the receptacle would be filled with hydrogel 18 and backing member 19 applied. The device would be allowed to sit until the volume above the pump 55 was filled and a steady flow from the needle 22 established. A longer start-up time is contemplated for this embodiment since a small void volume above pump 55 must be initially filled before steady flow is obtained. If the void volume is considered excessive, an additional spacer element of solid plastic chemically-resistant material can be introduced above pump 55 with formed passageway to provide fluid communication between outlets 58 and 20. After steady flow is verified the needle 22 would be inserted into the skin after it had been prepared in the conventional manner and the overlay applied as described above.

While FIG. 13 employs a spacer element 56 to permit one housing assembly to be used with various embodiments of the invention, it should be recognized that the spacer element is not a critical portion of the invention. Thus pump 55 could be used in like manner to pump 11 of FIG. 2 with the displacement membrane 16 being omitted. If this approach is taken it is preferable to redesign the configuration of the interior of the housing to minimize the void volume.

EXAMPLE

A pump assembly such as shown in FIGS. 7 and 8 for dispensing insulin was fabricated having a rotary syringe volume of 0.75 ml and a drug reservoir volume of 1.5 ml. The osmotic pump consisted of a tablet, 2.94 cm in diameter and 0.15 cm thick inclusive of a 0.038 cm coating of Eastman Kodak cellulose acetate E398-10 having a 0.4 cm diameter orifice in the upper surface. The core of the tablet consisted of 65% NaCl (by weight) 20% Polyox ® WRPA 3154 polyethylene oxide and 15% polyethylene glycol 20,000. The displacement membrane was formed from a 0.03 cm thick sheet of styrene butadiene copolymer elastomer. The housing was fabricated from a high impact polycarbonate resin with a maximum dimension at the base of 6.35 cm, a top surface of 2.86 cm in diameter and an overall height of approximately 1.45 cm. A 30 gauge needle was maintained at an angle of 15 to the base. Using a hydrogel as the source of actuating fluid the tonic flow rate of the device was approximately 10 μl/hour with a maximum duration of 150 hours. Each successive click (pulse) of the rotary syringe produced a pulse of 20 μl. Using U-100 insulin, this system delivered 2 U of insulin per pulse on top of a tonic delivery rate of 1 U/hr.

While the pumps of this have been described as being suitable for pumping fluid into the body at the site of the apparatus, the needle can obviously be replaced by a catheter or cannula for the delivery of the dispensed fluid to a location remote from the site at which the pump is worn. The cannula can be connected to the outlet port at one end and the other end may have a needle inserted directly into the body or may be attached to other apparatus such as a conventional IV-set by a Y-fitting so that the dosage delivered from the pump can be superimposed on another dosage form. Alternatively the outlet of the pump assembly could be connected to a nasopharyngal tube for example to administer a small amount of drug to the gastrointestinal tract or to a Foley catheter for delivery to the urinary bladder. Thus the specific purpose for which the delivered active agent is used is immaterial according to this invention, it being possible not only to directly administer to the body, but also to deliver it to a remote site for whatever purpose may be desired.

While this invention has been described with respect to a specific embodiment thereof, various modifications can be made by workers skilled in the art without departing from the scope of this invention which is limited only by the following claims wherein:

We claim:

1. A housing for a pump adapted to be mounted on the body of a subject, said housing comprising:
   (a) internal receptacle means open at the bottom, body proximal end, of said housing, said receptacle being defined by internal top and side surfaces,
   (b) exterior top and side surfaces, said exterior side surface tapering outwardly from said top surface,
   (c) an exterior bottom surface at the body proximal end of said exterior side surface and,
   (d) passageway means extending through said housing and terminating at one end proximate the internal top surface of said receptacle means and at another end proximate the body proximal end of said exterior side surface.

2. The pump housing of claim 1 wherein the body proximal end of said passageway means is provided with means to receive an infusion needle and to maintain said needle at an angle of 10° to 30° to the surface of the body on which it is to be mounted.

3. The pump housing of claim 2 wherein said angle is approximately 15°.

4. The pump housing of claim 1 wherein at least a portion of the housing defined by said top interior and exterior surfaces is transparent.

5. The pump housing of claim 1 wherein the intersection of the interior top and side walls defining said receptacle is radiused.

6. The pump housing of claim 5 wherein said second passageway means extends through said external top surface of said housing.

7. The pump housing of claim 1 further comprising second passageway means extending through said housing, the internal end of said second passageway means being in fluid communication with the upper portion of said receptacle whereby fluid may be charged into said receptacle.

8. A pump assembly adapted to be mounted on the body of a subject comprising, in combination:
(a) pump housing means, said housing means comprising:
  (i) internal receptacle means defined by the internal top and side surfaces of said housing;
  (ii) exterior top and side surfaces;
  (iii) an exterior bottom surface at the bottom, body proximal end of said exterior side surface; and
  (iv) passageway means extending through said housing and terminating at one end proximate the internal top surface of said receptacle means and at another end proximate the bottom end of said exterior side surface;
(b) an expansible, fluid impermeable membrane disposed within said receptacle means, dividing said receptacle means into upper and lower portions;
(c) fluid imbibing pump means in said lower portion, said pump means having outlet means in fluid communicating relationship with said membrane; and
(d) sealing means providing a fluid tight seal between said membrane, said fluid imbibing pump means and said housing means, whereby material discharged from said outlet means will be confined between said fluid imbibing pump means and said membrane.

9. The pump assembly of claim 8 further comprising a source of actuating fluid for said fluid imbibing pump means, said source being disposed in said lower portion of said receptacle and in contact with surface of said fluid imbibing pump means, whereby said fluid imbibing pump means will imbibe fluid from said source and discharge material through said outlet means between said fluid imbibing pump means and said membrane to cause said membrane to expand into the upper portion of said receptacle means.

10. The pump of claim 9 further comprising a fluid to be pumped confined within said upper portion of said receptacle means.

11. The pump of claim 10 wherein said fluid to be pumped is confined within a collapsable fluid impermeable bag received within said receptacle.

12. The pump of claim 11 wherein said membrane means is formed integrally with said bag.

13. The pump of claim 11 or 12 further comprising fluid conveying means providing fluid communication between the interior of said bag and said passageway means.

14. The pump of claim 9 further comprising reinforcing means for increasing the stiffness of said fluid imbibing pump.

15. The pump assembly of claim 8 further comprising means for generating a fluid pulse in fluid communication with the volume defined in said upper poriton of said receptacle means.

16. The pump of claim 15 wherein at least a portion of said means for generating a fluid pulse is formed as an integral part of said housing.

17. The pump assembly of claim 15 wherein said means for generating a fluid pulse is a unit discrete from said housing, having an outlet in fluid communication with the upper portion of said receptacle means.

18. The pump assembly of claim 15 wherein said pulse generator is a rotary syringe.

19. A pump assembly of claim 8 wherein at least the portion of said housing exterior top surface transparent.

20. The pump of claim 8 wherein the body proximal end of said passageway means carries a hollow needle at an angle of 10°–30° to the body surface.

21. The pump of claim 20 wherein said angle is 15°.

22. The pump assembly of claim 8, 9, 10, 15, 17, 18, 19, 20, or 21 wherein the exterior side surface of said pump housing means tapers outwardly from said top surface.

23. The pump of claim 8 further comprising reinforcing means for stiffening said fluid imbibing pump means.

24. The pump assembly of claim 8 wherein said membrane forms a portion of the wall of a collapsable bag containing a liquid to be pumped, said bag being configured to substantially fill the upper portion of said receptacle means.

25. The pump assembly of claim 24 wherein said bag is provided with a circumferentially extending self-sealing welt located to overlap the end of said pasageway means proximate the internal top surface of said receptacle whereby said bag may be filled and emptied by puncturing said welt with a hollow needle.

26. The pump assembly of claim 24 or 25 further comprising hollow puncturing mean associated with said passageway means, the internal end of which penetrates said bag at said welt.

27. The pump assembly of claim 24 wherein said bag is provided with a circumferentially extending self-sealing welt located to overlap the body distal end of said passageway means.

28. The pump assembly of claims 24 or 27 further comprising a hollow puncturing means associated with said passageway means puncturing said bag at said welt.

29. A body mounted pump assembly comprising in combination
(a) a housing having outer top and side walls, said side walls flaring outwardly from said top wall whereby the circumference of the base of said housing is greater than the top of said housing;
(b) receptacle means, defined within said housing and disposed below said top wall, the side surface of said receptacle means being provided with a circumferential shoulder, dividing said receptacle means into an upper and a lower portion,
(c) a fluid imbibing pump disposed in said lower portion of said receptacle with its outlet directed towards said upper portion
(d) means for maintaining said fluid imbibing pump in fluid sealing relationship to said shoulder and
(e) passageway means extending through said side wall from a point proximate its lower outer end into the upper portion of said receptacle means.

30. The pump assembly of claim 29 wherein the outer end of said passageway is provided with a hollow needle maintained at an angle of from 10° to 30° to the plane of the basal surface of said housing.

31. The pump assembly of claim 30 wherein said angle is approximately 15°.

32. The pump assembly of claim 29 wherein at least that portion of the top wall of said housing above said receptacle means is transparent.

33. The pump assembly of claim 29 further comprising an elastic membrane disposed above said fluid imbibing pump and in fluid sealing relationship to said shoulder and said pump.

34. The pump assembly of claim 33 wherein said membrane is a portion of a liquid containing bag received within said upper portion of said receptacle.

35. The pump assembly of claims 33 or 34 further comprising support means disposed under said fluid imbibing pump and in stiffening relationship thereto.

36. The pump assembly of claim 35 further comprising a source of activating fluid for said fluid imbibing pump in said lower portion of said receptacle and in contact with the exterior of said fluid imbibing pump.

37. The pump assembly of claim 36 further comprising fluid impermeable means closing the body proximal end of said receptacle, whereby said source of fluid is maintained in said receptacle and contact of said fluid with the surface of the body to which it is applied is prevented.

38. The pump assembly of claim 34 wherein the outer surface of said bag is in sealing relationship to said inner end of said passageway means.

39. The pump assembly of claim 38 further comprising means for puncturing said bag to permit discharge of the fluid contents through said passageway means.

40. The pump assembly of claim 29 further comprising means for providing a fluid pulse in fluid communicating relationship to said upper portion of said receptacle.

41. The pump assembly of claim 40 wherein said means is a rotary syringe.

42. The pump assembly of claims 29, 30, 32, 33, 34, 39, 40 further comprising a source of activating fluid for said fluid imbibing pump in said lower portion of said receptacle and in contact with the exterior of said fluid imbibing pump.

43. The pump assembly of claim 42 further comprising fluid impermeable means closing the body proximal end of said receptacle and maintaining said source of fluid in said receptacle and preventing contact of said fluid with the surface of the body to which it is applied.

44. A housing for a pump adapted to be mounted on the body of a subject, said housing comprising, in combination:
   (a) internal receptacle means open at the bottom, body proximal, end of said housing, said receptacle being defined by internal top and side surfaces;
   (b) exterior top and side surfaces, said exterior side surface tapering outwardly from said top surface;
   (c) an exterior bottom surface at the body proximal end of said exterior side surface;
   (d) first and second passageway means extending through said housing, each said passageway means terminating at one end proximal to the internal top surface of said receptacle means and at the other end proximate the body proximal end of said exterior side surface.

45. The housing of claim 44 wherein one of said passageways means is provided with self sealing means through which fluid to be dispensed from said pump may be charged into said receptacle means.

46. The housing of claim 44 wherein at least a portion of said housing defined by said internal and external surfaces is transparent.

47. A pump assembly adapted to be mounted on the body of the subject said assembly comprising, in combination:
   (a) internal receptacle means open at the bottom, body proximal, end of said housing, said receptacle being defined by internal top and side surfaces;
   (b) exterior top and side surfaces, said exterior side surface tapering downwardly from said top surface;
   (c) an exterior bottom surface at the body proximal end of said exterior side surface,
   (d) passageway means extending through said housing and terminating at one end proximate the internal top surface of said receptacle means and at another end proximate the body proximal end of said exterior side surface;
   (e) fluid imbibing pump means within said internal receptacle means said fluid imbibing pump means having an outlet in fluid communication with said passageway means;
   (f) means for maintaining fluid tight seal between the exterior of said fluid imbibing pump means and the internal surface of said receptacle means; and
   (g) a source of activating fluid for said fluid imbibing pump said source of said activating fluid being received within said receptacle and in contact with the exterior surface of said fluid imbibing pump means; whereby said activating fluid may be imbibed into said fluid imbibing pump means and the flud discharged through the outlet of said fluid imbibing pump means will flow out of said pump assembly through said passageway means.

48. The pump assembly of claim 47 where at least a portion of the top of said internal receptacle means is transparent.

* * * * *